United States Patent [19]

Lohr

[11] 4,246,131
[45] Jan. 20, 1981

[54] LOW-IRRITANT SURFACTANT COMPOSITION

[75] Inventor: John W. Lohr, Cherry Hill, N.J.

[73] Assignee: Inolex Corporation, Chicago, Ill.

[21] Appl. No.: 961,972

[22] Filed: Nov. 20, 1978

Related U.S. Application Data

[62] Division of Ser. No. 768,203, Feb. 14, 1977, Pat. No. 4,137,191.

[51] Int. Cl.$^3$ .......................... C11D 1/10; C11D 7/50
[52] U.S. Cl. ..................................... 252/153; 252/545;
252/546; 252/550; 252/551; 252/555;
252/DIG. 13; 252/DIG. 14
[58] Field of Search ............... 252/153, 545, 546, 547,
252/550, 551, 555, DIG. 5, DIG. 7, DIG. 13,
DIG. 14

[56] References Cited

U.S. PATENT DOCUMENTS

| | | | |
|---|---|---|---|
| 3,870,647 | 3/1975 | Travers | 252/118 |
| 3,928,251 | 12/1975 | Bolich et al. | 252/545 |
| 3,950,417 | 4/1976 | Verdicchio et al. | 252/545 |
| 3,957,970 | 5/1976 | Korkis | 424/70 |
| 4,166,048 | 8/1979 | Nishimura et al. | 252/546 |

FOREIGN PATENT DOCUMENTS

| | | | |
|---|---|---|---|
| 1277495 | 9/1968 | Fed. Rep. of Germany | 252/545 |
| 2457239 | 6/1975 | Fed. Rep. of Germany | 252/546 |
| 50-76106 | 6/1975 | Japan | 252/546 |
| 51-37102 | 3/1976 | Japan | 252/548 |
| 708000 | 4/1954 | United Kingdom | 252/153 |
| 1128836 | 10/1968 | United Kingdom | 252/DIG. 7 |

OTHER PUBLICATIONS

Lehne, R. K., "Specialty Polyols," *American Perfumer and Cosmetics*, vol. 78, Oct., 1963, pp. 103–106.

*Primary Examiner*—P. E. Willis, Jr.
*Attorney, Agent, or Firm*—Dressler, Goldsmith, Shore, Sutker & Milnamow, Ltd.

[57] ABSTRACT

A low irritant surfactant composition particularly adapted for shampoos and other light duty cleansing applications, comprising substantially equimolar amounts of a betaine surfactant and an amine fatty alcohol sulfate or sulfonate in a high boiling water miscible, polar, organic liquid. Preferably, the betaine is of the formula:

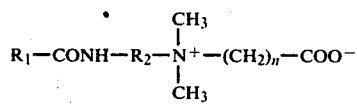

wherein $R_1$ is a long chain alkyl group and $R_2$ is a short chain alkylene group, and n is an integer from 1 to 3; and the betaine is prepared in a reaction system containing the organic liquid. The alkanolamine fatty alcohol sulfate or sulfonate is then added to the system in an equimolar amount, or preferably prepared in situ in the reaction medium by the reaction of an amine with a long chain alkyl monoester of sulfuric acid.

14 Claims, No Drawings

LOW-IRRITANT SURFACTANT COMPOSITION

This is a division of application Ser. No. 768,203, filed Feb. 14, 1977 now U.S. Pat. No. 4,137,191.

BACKGROUND OF THE INVENTION

Betaines of the formula:

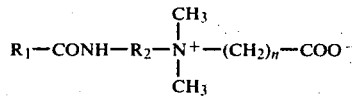

wherein $R_1$ is a long chain alkyl group, $R_2$ is a short chain alkylene group, and n is an integer from 1 to 3 are known, and they are known to be useful in shampoo compositions. These specific betaine compounds and their preparation are discussed in U.S. Pat. Nos. 2,866,423 and 3,225,074 and in West German Pat. No. 1,062,392; and the latter also discloses the use of such compounds in shampoo and bubble bath preparations. Related compounds are also disclosed in U.S. Pat. No. 2,777,872 and in U.S. Pat. No. 2,961,451.

The betaine compounds are disclosed as prepared by the reaction of an amidotertiary amine of the formula:

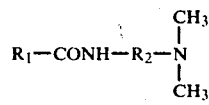

wherein $R_1$ and $R_2$ have the meanings stated above with an alkali metal salt of a short chain chloroalkanoic acid, such as chloroacetic acid, in an aqueous medium, or in a medium which includes water and an organic solvent.

An alkali metal chloride, such as sodium chloride, is produced as a co-product in the process, and this co-product is difficult or expensive to remove from substantially aqueous reaction media.

Other betaine surfactants are made in a similar manner by the substitution of other tertiary amines having at least one long chain aliphatic radical attached directly to the amino nitrogen atom for the amidotertiary amine of the above formula.

The betaine products have desirable foaming and cleansing properties, and are generally regarded as being mild in their action. They, however, result in compositions that are inherently moderately irritating to the eyes when used at concentrations normally considered effective in enhancing foaming and conditioning properties of commercial shampoo.

SUMMARY OF THE INVENTION

In accordance with the instant invention, the aforementioned reaction between the tertiary amine, and preferably the amidotertiary amine, and the chloroacetic acid salt is carried out in a water-free medium comprising a water-miscible, polar, organic solvent having a boiling point of at least 180° C.; and most of the co-product alkali metal chloride, as it is formed, goes into a separate solid phase whence it can be readily removed by decantation, filtration, or centrifugation. For convenience, the invention will be described herein primarily with respect to its preferred embodiment in which the tertiary amine is an amidotertiary amine and the betaine has a long chain amidoalkyl group attached to a positively charged nitrogen atom.

An anionic surfactant material in the form of an alkanolamine fatty alcohol sulfate or sulfonate, is then added to the betaine product in its non-aqueous polar, organic liquid reaction medium, preferably made in situ by the reaction of a fatty alcohol monoester of sulfuric acid or a sulfonic acid with an alkanolamine in such proportions as hereinafter set forth that the resulting balanced blend, which when simply diluted with water and combined with suitable adjuvants such as fragrance, color and preservative, results in a shampoo having desirable aesthetic properties, and which also exhibits markedly reduced eye irritation scores when compared to shampoos of similar active content, randomly formulated to contain combinations of like ingredients outside of composition ranges shown, but which have otherwise similar characteristics and which are otherwise effective in performance.

The first three of the following examples constitute a stepwise description of a preferred method of preparing one desired composition which may be so utilized. Example 4 describes an alternative preparation of the final product.

EXAMPLE 1

Preparation of Tertiary Amido-amine

One mol of refined bleached deodorized coconut oil was reacted with three mols of dimethylaminopropylamine until there was no further change in amine number on checking successive samples of the reaction mass. This indicated substantially complete reaction of the primary amine group of the dimethylaminopropylamine by formation of cocoamidopropyl dimethylamine and co-product glycerine. The product had an amine number of 174 indicating a gross combining weight of 322 including the co-product glycerine which remained in homogeneous solution. The product was thus composed of 874 parts (90.5%) of cocoamidopropyl dimethylamine (combining weight—291.3) together with 92 parts (9.5%) of glycerine.

EXAMPLE 2

Preparation of Cocoamidopropyl Betaine 9.60 parts by weight of propylene glycol was weighed into an open stainless steel vessel and 10.56 parts of the cocoamidopropyl dimethylamine of Example 1 together with its dissolved glycerine was added and dissolved. The mixture was heated with stirring to 80° C. at which point 3.83 parts of sodium chloroacetate powder (sufficient to form 1.95 parts of co-product sodium chloride) was added with continued stirring over a period of 15 minutes. External heating was discontinued. The exothermic reaction began almost immediately, and within 25 minutes after complete addition, the temperature of the mass has risen to 112° C. after which cooling by radiation began at a rate of about 20° C. per hour.

Heating was resumed when the reaction mass temperature had fallen to 82° C. and the mass was maintained at 82° C. for an additional 3 hours before being allowed to cool.

At no time was the reaction mass homogeneous. That is, there was no visual change during the course of the reaction. The product appeared generally tannish and contained a finely divided suspended solid phase. At the end of the reaction period, when the mass had cooled to room temperature, the vessel together with its contained reaction product was reweighed and 0.25 parts of propylene glycol was added to restore evaporation loss. The addition was thoroughly incorporated in the reacted mass which was then filtered to separate the suspended solids.

The final clear product (22.36 parts) contained 3.19% of sodium chloride. The cake (1.63 parts) contained 77.72% of sodium chloride as a solid salt together with adhering reaction product. The material balance, calculated from analysis and product yields, was as follows:

| MATERIALS CHARGED | | PARTS BY WEIGHT |
|---|---|---|
| Propylene glycol | | 9.60 |
| Cocoamidopropyl dimethylamine | | 10.56 |
| Sodium chloroacetate | | 3.83 |
| | TOTAL | 23.99 |
| PRODUCTS CLEAR FILTERED BETAINE CONC. | % 100.0 | |
| Containing: | | |
| Propylene Glycol | 42.17 | 9.429 |
| Betaine | 50.32 | 11.252 |
| Glycerine | 4.32 | 0.966 |
| Na Cl | 3.19 | 0.713 |
| | | 22.360 |

The amount of sodium chloride produced, based on the weights of recovered products and their chloride analyses was found to be 1.98 parts, and, since the sodium chloride theoretically available was calculated to be 1.95 parts, complete hydrolysis of the charged sodium chloroacetate had taken place. The resulting liquid product has a pH of 6.49 in 10% aqueous solution.

EXAMPLE 3

Preparation of Ionically Balanced Surfactant

The molecular weight of the betaine prepared in Example 2 was calculated to be 349.3 so that it was determined that (349.3/0.5032) or 694.6 grams of reaction product contained one gram-mol of active betaine. Diethanolamine lauryl sulfate made from the conventional lauryl alcohol of commerce has a molecular weight of 385. Thus, to prepare an ionically balanced detergent concentrate containing equimolar amounts of diethanolamine lauryl sulfate and the betaine, 385 parts of the former was dissolved in 694.16 parts of betaine concentrate of Example 2 forming 1079.16 parts of an equimolar anionic-amphoteric blended (ionically balanced) detergent concentrate containing in excess of 68% surface active substances. The product was a viscous, slightly hazy, amber fluid having a pH of 5.95 in 10% aqueous solution.

EXAMPLE 4

Alternative Preparation of Ionically Balanced Surfactant

Example 3 was repeated, except that the diethanolamine lauryl sulfate was neutralized in situ rather than added as such. Specifically, 105 parts of diethanolamine was added to 694.6 parts of the betaine reaction product of Example 2 in a first reaction vessel. In a second reaction vessel, 80 parts of sulfur trioxide was reacted with 200 parts of commercial lauryl alcohol having a hydroxyl value of 280.5 and an average molecular weight of 200.3 to form the monolauryl ester of sulfuric acid. This said monolauryl ester of sulfuric acid was then removed from the said second reaction vessel and transferred to the first reaction vessel and commingled with the contents thereof to form the required quantity of diethanolamine lauryl sulfate in situ.

The ionically balanced surfactant concentrate prepared by the method of Example 4 is aesthetically preferable for the formulation of consumer products because it contains lesser amounts of inorganic sulfate contaminants which are frequently found in diethanolamine lauryl sulfate and which generally result from the preparation of the latter in aqueous media.

While the process of Example 4 produces an excellent product when the reactants are substantially dry and there are no hydrolysis side reactions, the presence of moisture in any of the reactants, or the introduction of moisture during the handling thereof, necessitates some departure from the theoretical stoichiometric proportions if low irritation levels in the first product are to be maintained.

It is well known in the art that lauryl sulfuric acid is unstable and that hydrolysis to alcohol and sulfuric acid takes place fairly rapidly in the presence of even small amounts of water. To the extent that water is present in the reaction mix or is introduced as a contaminant in the starting alcohol or is formed as the result of uncontrolled and undesirable oxidation side reactions, sulfuric acid will be present in the lauryl sulfuric acid. Furthermore, each molecule of sulfuric acid thus formed will require two equivalents of diethanolamine (DEA) for neutralization so that any excess of DEA required for neutralization is a direct measure of both the $(DEA)_2.H_2SO_4$ formed and the equivalent or molar deficiency of the anionic active alkyl sulfate.

Alkanolamine lauryl sulfate products containing lauryl sulfuric acid hydrolysis products and thus deficient in anionic active agent when blended with the betaine in amounts calculated as stoichiometric for pure alkanolamine lauryl sulfate exhibit higher irritation levels than desired. To a lesser extent, the irritation levels are still high, even after the anionic-amphoteric balance is exactly restored by the addition of one equivalent of added betaine for each equivalent of diethanolamine sulfate. It has been found that it takes 1.5 to 2.0 equivalents of betaine for each equivalent of diethanolamine sulfate to produce a blended product having optimum low irritation levels although 1.0 to 3.0 equivalents of betaine may be used when somewhat higher irritation levels can be tolerated.

In general, the amounts of betaine and the anionic surfactant should be close to equimolar. Molar proportions of betaine to anionic surfactant in the range of about 1.0:1 to about 1.25:1 are suitable.

While the invention has been described primarily with respect to fatty acid amidopropyl betaines, it is to be understood that other betaine surfactant compounds may be employed having at least one long chain aliphatic radical attached directly to a positively charged nitrogen atom. Suitable betaines include those of the formula:

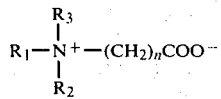

wherein $R_1$ is an alkyl group having 8 to 18 carbon atoms, $R_2$ and $R_3$ are independently selected from alkyl and hydroxyalkyl groups containing up to 3 carbon atoms and n is an integer from 1 to 3. Compounds of this type may be prepared by the reactions described in U.S. Pat. No. 2,129,264.

In place of diethanolamine lauryl sulfate as the anionic surfactant, other anionic sulfates or sulfonates may be used of the group consisting of alkanolamine neutralized fatty acid sulfates derived from $C_8$ to $C_{18}$ alcohols, alkyl ether sulfates containing 1 to 4 alkylene oxide groups and an alkyl group having 8 to 18 carbon atoms and alkyl sulfonates and alkenyl sulfonates in the surfactant range containing 10 to 18 carbon atoms in the alkyl chain.

In place of propylene glycol as the reaction medium for the preparation of the betaine and as the solvent for the final blend, other water-miscible, polar organic liquids may be used which have a boiling point of at least 180° C., including ethylene glycol, glycerine, hexylene glycol, diethylene glycol, triethylene glycol, dipropylene glycol and other water-miscible ether or polyether polyols, or mixtures thereof.

The reaction medium should preferably be used in a limited amount so that the total amount of betaine and anionic surfactant, together, comprises at least 40% by weight of the composition. In this concentrated form, the composition may be stored and shipped as a water-free concentrate to minimize storage and shipping expenses. It may also, if desired, be stored and shipped in a concentrate prepared by adding a small amount of water, e.g. up to about 10% by weight, to the water-free concentrate.

Either the water-free or the water-containing concentrate described above may be formulated into a substantially irritation-free shampoo by the addition of water, and optionally the addition of perfume, coloring, or hair conditioning materials. For shampoos, it is preferred that water constitute at least 60 weight percent of the composition and that the composition have a pH between about 6.0 and about 8.0.

The foregoing specification is intended to be illustrative and is not to be taken as limiting. Other variations and modifications of the invention are possible without departing from the spirit and scope thereof.

We claim:

1. A substantially water-free low irritant surfactant composition in fluid form comprising a mixture of a betaine surfactant compound having at least one long chain aliphatic radical attached directly to a positively charged nitrogen atom and an anionic surfactant of the group consisting of alkanolamine neutralised fatty alcohol sulfates derived from $C_8$ to $C_{18}$ alcohols, alkyl ether sulfates containing 1 to 4 ethylene oxide groups and an alkyl group having 8 to 18 carbon atoms, and alkyl sulfonates and alkenyl sulfonates in the surfactant range containing 10 to 18 carbon atoms in the alkyl chain; said surfactant mixture being dispersed in a non-aqueous liquid medium comprising a water-miscible, polar, organic liquid having a boiling point of at least 180 C., said betaine surfactant compound and said anionic surfactant being present in molar proportions from about 1.0:1 to about 1.25:1, comprising together at least 40 weight percent of said compositions and comprising the sole surfactant materials in said composition.

2. The composition of claim 1 wherein said surfactant mixture is dispersed in said non-aqueous liquid medium as a solution.

3. The composition of claim 1 wherein said anionic surfactant comprises an alkanolamine neutralized fatty alcohol sulfate and contains a minor amount of alkanolamine sulfate neutralized by 1.0 to 3.0 equivalents of betaine for each equivalent of alkanolamine sulfate.

4. The composition of claim 1 wherein said betaine has the formula

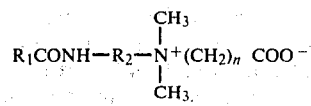

where $R_1$ is an alkyl group having from 7 to 17 carbon atoms and $R_2$ is an alkylene group having from 2 to 4 carbon atoms and n is an integer from 1 to 3.

5. The composition of claim 1 wherein said betaine has the formula

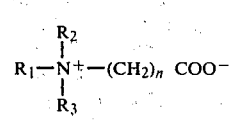

where $R_1$ is an alkyl group having 8 to 18 carbon atoms, $R_2$ and $R_3$ are independently selected from alkyl and hydroxyalkyl groups containing up to 3 carbon atoms and n is an integer from 1 to 3.

6. The composition of claim 1 wherein said water-miscible, polar, organic liquid is a polyol of the group consisting of ethylene glycol, propylene glycol, glycerine, hexylene glycol, hexamethylene glycol, diethylene glycol, triethylene glycol, dipropylene glycol and mixtures thereof.

7. The composition of claim 1 wherein said anionic surfactant is diethanolamine lauryl sulfate.

8. The composition of claim 7 wherein said diethanolamine lauryl sulfate is made in situ by the reaction of lauryl sulfuric acid with diethanolamine in the presence of said betaine and said water-miscible, polar, organic liquid.

9. The composition of claim 1 wherein said betaine is N-cocoamidopropyl-N,N-dimethyl-N-carboxymethylammonium betaine.

10. A substantially water-free low irritant surfactant composition in fluid form comprising substantially equimolar amounts of N-cocoamidopropyl-N,N-dimethyl-N-carboxymethylammonium betaine and diethanolamine lauryl sulfate in propylene glycol, said betaine and said diethanolamine lauryl sulfate together comprising at least 40 percent by weight of said composition and comprising the sole surfactant materials in said composition.

11. A shampoo composition containing the composition of claim 10 and containing at least 60 weight percent of water, said composition having a pH between about 6.0 and about 8.0.

12. A shampoo concentrate comprising from zero to about 10 weight percent of water and from about 90 to 100 weight percent of a substantially water-free low irritant surfactant composition in fluid form comprising a mixture of substantially equimolar amounts of a betaine surfactant compound having at least one long chain aliphatic radical attached directly to a positively charged nitrogen atom and an anionic surfactant of the group consisting of alkanolamine neutralised fatty alcohol sulfates derived from $C_8$ to $C_{18}$ alcohols, alkyl ether sulfates containing 1 to 4 ethylene oxide groups and an alkyl group having 8 to 18 carbon atoms, and alkyl sulfonates and alkenyl sulfonates in the surfactant range containing 10 to 18 carbon atoms in the alkyl chain; said surfactant mixture being dispersed in a non-aqueous liquid medium comprising a water-miscible, polar, organic liquid having a boiling point of at least 180° C. and said betaine surfactant compound together with said anionic surfactant comprising at least 40 weight percent of said surfactant composition and comprising the sole surfactant materials in said surfactant composition.

13. A shampoo comprising at least 60 percent by weight of water and up to 40 percent by weight of a substantially water-free low irritant surfactant composition in fluid form comprising a mixture of substantially equimolar amounts of a betaine surfactant compound having at least one long chain aliphatic radical attached directly to a positively charged nitrogen atom and an anionic surfactant of the group consisting of alkanolamine neutralized fatty alcohol sulfates derived from $C_8$ to $C_{18}$ alcohols, alkyl ether sulfates containing 1 to 4 ethylene oxide groups and an alkyl group having 8 to 18 carbon atoms, and alkyl sulfonates and alkenyl sulfonates in the surfactant range containing 10 to 18 carbon atoms in the alkyl chain; said surfactant mixture being dispersed in a non-aqueous liquid medium comprising a water-miscible, polar, organic liquid having a boiling point of at least 180° C. and said betaine surfactant compound together with said anionic surfactant comprising at least 40 weight percent of said surfactant composition and comprising the sole surfactant materials in said surfactant composition.

14. A shampoo comprising at least 60 percent by weight of water and up to 40 percent by weight of a substantially water-free low irritant surfactant composition in fluid form comprising substantially equimolar amounts of N-cocoamidopropyl-N,N-dimethyl-N-carboxymethylammonium betaine and diethanolamine lauryl sulfate in propylene glycol, said betaine and said diethanolamine lauryl sulfate together comprising at least 40 percent by weight of said surfactant composition and comprising the sole surfactant materials in said surfactant composition, said shampoo having a pH between about 6.0 and about 8.0.

* * * * *

UNITED STATES PATENT OFFICE
CERTIFICATE OF CORRECTION

Patent No. 4,246,131    Dated Jan. 20, 1981

Inventor(s) John Lohr

It is certified that error appears in the above-identified patent and that said Letters Patent are hereby corrected as shown below:

Column 3, line 25, the following should appear as part of the tabulation above the horizontal line marking the end of the tabulation:

SALT CAKE

Containing:

| | | |
|---|---|---|
| Na Cl (Solid) | 76.99 | 1.255 |
| Propylene Glycol | 9.71 | 0.158 |
| Betaine | 11.58 | 0.189 |
| Glycerine | 0.99 | 0.016 |
| Na Cl (Dissolved) | 0.73 | 0.012 |
| | | 1.630 |

Signed and Sealed this

Twenty-sixth Day of May 1981

[SEAL]

Attest:

RENE D. TEGTMEYER

Attesting Officer    Acting Commissioner of Patents and Trademarks